US010379041B2

(12) United States Patent
Guillaume et al.

(10) Patent No.: US 10,379,041 B2
(45) Date of Patent: Aug. 13, 2019

(54) METHOD FOR DETERMINING THE QUALITY OF A SEMEN OF A VERTEBRATE ANIMAL

(71) Applicant: Union Evolution, Rennes (FR)

(72) Inventors: Francois Guillaume, Rennes (FR); Maena Le Corvec, Maxent (FR); Thomas De Bretagne, Breal sous Montfort (FR); Gildas Michel, Montfort sur Meu (FR); Stephane Basquin, Saint Aubin du Cormier (FR); Frederic Charreaux, Saint Etienne de Montlue (FR); Hughes Tariel, Rennes (FR); Benoit Guyonnet, Rennes (FR)

(73) Assignee: UNION EVOLUTION, Rennes (FR)

( * ) Notice: Subject to any disclaimer, the term of this patent is extended or adjusted under 35 U.S.C. 154(b) by 0 days.

(21) Appl. No.: 15/770,374

(22) PCT Filed: Oct. 15, 2016

(86) PCT No.: PCT/FR2016/052671
§ 371 (c)(1),
(2) Date: Apr. 23, 2018

(87) PCT Pub. No.: WO2017/068266
PCT Pub. Date: Apr. 27, 2017

(65) Prior Publication Data
US 2018/0313751 A1 Nov. 1, 2018

(30) Foreign Application Priority Data

Oct. 21, 2015 (FR) ..................................... 15 60026
Jul. 21, 2016 (FR) ..................................... 16 56931

(51) Int. Cl.
*G01N 33/487* (2006.01)
*G01N 21/3577* (2014.01)
(Continued)

(52) U.S. Cl.
CPC ......... *G01N 21/3577* (2013.01); *A01K 67/02* (2013.01); *G01N 21/35* (2013.01); *G01N 33/487* (2013.01)

(58) Field of Classification Search
CPC .. G01N 21/3577; G01N 21/31; G01N 33/487; A01K 67/02
See application file for complete search history.

(56) References Cited

U.S. PATENT DOCUMENTS

| 3,377,374 A | 4/1968 | Hale et al. |
| 6,280,381 B1 * | 8/2001 | Malin ................ A61B 5/14532 128/920 |

(Continued)

FOREIGN PATENT DOCUMENTS

| CN | 103698310 A | 4/2014 |
| FR | 1450661 A | 7/1964 |

(Continued)

OTHER PUBLICATIONS

Abraham Savitzky, "Smoothing and Differentiation of Data by Simplified Least Squares Procedures", 1964.*
(Continued)

*Primary Examiner* — Maurice C Smith
(74) *Attorney, Agent, or Firm* — David D. Brush; Westman, Champlin & Koehler, P.A.

(57) ABSTRACT

A method is provided for determining quality of semen of a vertebrate animal. The method includes the following steps: measuring at least one absorption spectrum of a sample of the semen; selecting a number n of wave numbers $\sigma_{j\ (j \in [1;n])}$ which are characteristic of the semen of the breed or of the species of the animal; determining from the absorption spectrum or spectra of a value of the absorption $X_j$ and/or a value of the second derivative of the absorption $X_j''_{(j \in [1;n])}$ for each of the n wave numbers $\sigma_{j\ (j \in [1;n])}$; and calculating a non-return rate Y at a predefined number of days from the (Continued)

absorption values $X_j$ and/or from the second derivative of the absorption $X_j''$ previously determined.

20 Claims, 4 Drawing Sheets (51) Int. Cl.
*A01K 67/02* (2006.01)
*G01N 21/35* (2014.01)

(56) References Cited

U.S. PATENT DOCUMENTS

| | | | |
|---|---|---|---|
| 6,493,566 B1* | 12/2002 | Ruchti | A61B 5/0059 600/309 |
| 7,524,681 B2* | 4/2009 | Wolf | G01N 21/3563 250/343 |
| 9,134,252 B2 | 9/2015 | Tariel | |
| 2004/0146848 A1* | 7/2004 | Kislev | B01L 3/502 435/4 |
| 2013/0102066 A1 | 4/2013 | Bureau et al. | |
| 2013/0331693 A1* | 12/2013 | Moreno | A61D 19/027 600/437 |
| 2014/0128691 A1* | 5/2014 | Olivier | A61B 5/0833 600/301 |

FOREIGN PATENT DOCUMENTS

| | | |
|---|---|---|
| FR | 2958403 B1 | 4/2010 |
| WO | 2013017324 A1 | 2/2013 |
| WO | 2013064159 A1 | 5/2013 |

OTHER PUBLICATIONS

Farrell P.B., "Quantification of Bull Sperm Characteristics measured by Computer-Assisted Sperm Analysis (CASS) and the Relationship to fertility", 1997, Elsevier.*
American Angus Association, "Suggested Sale Terms and Conditions", Feb. 21, 2014, Breeder's Reference Guide.*
Daniel Filipe Cruz et al. "Oxidative Stress Markers: Can they be used to evaluate human sperm quality?" Turkish Journal of Urology, 41(4), Oct. 14, 2015.
Amir Abramovich et al. "Diagnostic and Analysis of Human Sperm Characteristics Using Fourier Transform Infrared Spectroscopy." Open Journal of Urology, vol. 5, No. 6. Jun. 30, 2015.
C.C. Perez-Mahn et al. "Assessment of Porcine Semen Concentration by Near InfraRed Spectroscopy (NIRS)." Reproduction in Domestic Animals, Blackwell Wiss. Verlag, Berlin, vol. 42, No. Supplement 2. Sep. 1, 2007.
P.B. Farrell et al. "Quantification of Bull Sperm Characteristics Measured by Computer-Assisted Sperm Analysis (CASA) and the Relationship to Fertility." Theriogenology, vol. 49, No. 4. Mar. 1, 1998.
J. M. DeJarnette et al. "Understanding Estimates of AI Sire Fertility." Select Sires. 2010.
"WHO Laboratory Manual for the Examination and Processing of Human Semen: Fifth Edition." World Health Organization. 2010.
Christopher De Jonge, PhD. "Semen Analysis: Looking for an Upgrade in Class." Fertility and Sterility, vol. 97, No. 2. Feb. 2012.
JP Kastelic et al. "Breeding Soundness Evaluation and Semen Analysis for Predicting Bull Fertility." Reprod Dom Anim 43 (Suppl. 2), Blackwell Verlag. 2008.
E. Moce et al. "In vitro Evaluation of Sperm Quality." Animal Reproduction Science 105 (2008). Nov. 26, 2007.
Jean-Louis Dacheux et al. "New insights into epididymal function in relation to sperm maturation." Society for Reproduction and Fertility. 2014.
William V. Holt et al. "Concepts in sperm heterogeneity, sperm selection and sperm competition as biological foundations for laboratory tests of semen quality." Society for Reproduction and Fertility 2004.
H. Rodriguez-Martinez. "Can We Increase the Estimative Value of Semen Assessment?" Reprod Dom Anim 41 (Suppl.2), Blackwell Verlag. 2006.
Anna M. Petrunkina et al. "Functional significance of responsiveness to capacitating conditions in boar spermatozoa." Theriogenology 64. 2005.
R.P. Amann et al. "In Vitro Evaluation of Sperm Quality: An Opinion." Journal of Andrology, vol. 14, No. 6. Nov./Dec. 1993.
J.K. Graham et al. "Fertility evaluation of frozen/thawed semen." Theriogenology 64. 2005.
A. Januskauskas et al. "ASsessment of Sperm Characteristics Post-Thaw and Response to Calcium Ionophore in Relation to Fertility in Swedish Dairy AI Bulls." Theriogenology 53:859-875. 2000.
James K. Graham. "Assessment of sperm quality: a flow cytometric approach." Animal Reproduction Science 68. 2001.
Rocio Rivera Egea et al. "OMICS: Current and future perspectives in reproductive medicine and technology." Journal of Human Reproductive Sciences 7(2). Apr.-Jun. 2014.
C. Robert. "Challenges of functional genomics applied to farm animal gametes and pre-hatching embryos." . Theriogenology 70. 2008.
Jeffrey J. Jones et al. "Strategies and Data Analysis Techniques for Lipid and Phospholipid Chemistry Elucidation by Intact Cell MALDI-FTMS." American Society for Mass Spectrometry. Sep. 25, 2004.
Valerie Labas et al. Analysis of epididymal sperm maturation by MALDI profiling and top-down mass spectrometry. Journal of Proteomics 113. 2015.
D. Helm et al. "Classification and identification of bacteria by Fourier-transform infrared spectroscopy." Journal of General Microbiology 137. 1991.
Ivonne Stamm et al. "Yersinia enterocolitica in Diagnostic Fecal Samples from European Dogs and Cats: Identification By Fourier Transform Infrared Spectroscopy and Matrix-Assisted Laser Desorption Ionization—Time of Flight Mass Spectrometry." Journal of Clinical Microbiology, vol. 51, No. 3. Mar. 2013.
Juergen Backhaus et al. "Diagnosis of breast cancer with infrared spectroscopy from serum samples." Vibrational Spectroscopy 52. Feb. 2, 2010.
Angela Kallenbach et al. "Immunohistochemistry, histopathology and infrared spectral histopathology of colon cancer issue sections." Journal of Biophotonics. Dec. 10, 2012.
Paul D. Lewis et al. "Evaluation of FTIR Spectroscopy as a diagnostic tool for lung cancer using sputum." BMC Cancer. 2010.
J.M.G. Canvin et al. "Infrared spectroscopy: shedding light on synovitis in patients with rheumatoid arthritis." British Rheumatology 42 . 2003.
Brum Mara Aparecida et al. "Rapid detection of whey in milk powder samples by spectrophotometric and multivariate calibration." Food Chemistry 174. Nov. 8, 2015.
Con Mallidis et al. "Raman microspectroscopy: shining a new light on reproductive medicine." Human Reproduction Update, vol. 20, No. 3 pp. 403-414. Oct. 21, 2013.
C. Mallidis et al. "In situ visualization of damaged DNA in human sperm by Raman microspectroscopy." Human Reproduction, vol. 26, No. 7 pp. 1641-1649. 2011.
Zufang Huang et al. "Raman spectroscopic characterisation and differentiation of seminal plasma." Journal of Biomedical Optics, vol. 16(11). Nov. 2011.
French Search Report dated Sep. 6, 2016, for corresponding French Application No. 1560026, filed Oct. 21, 2015.
International Search Report dated Mar. 15, 2017, for corresponding International Application No. PCT/FR2016/052671, filed Oct. 15, 2016.
Written Opinion of the International Searching Authority dated Mar. 24, 2017, for corresponding International Application No. PCT/FR2016/052671, filed Oct. 15, 2016.

* cited by examiner

METHOD FOR DETERMINING THE QUALITY OF A SEMEN OF A VERTEBRATE ANIMAL

1. CROSS-REFERENCE TO RELATED APPLICATIONS

This Application is a Section 371 National Stage Application of International Application No. PCT/FR2016/052671, filed Oct. 15, 2016, the content of which is incorporated herein by reference in its entirety, and published as WO 2017/068266 on Apr. 27, 2017, not in English.

2. FIELD OF THE INVENTION

The invention relates to the field of breeding and in particular to breeding cattle, avians and fish.

More specifically, the invention relates to a method for determining the quality of a semen of a vertebrate animal The invention finds particular application in the selection of a quality semen to improve the success rate of an insemination of an animal in a breeding operation or in the control of the quality of the semen of breeding stock.

3. STATE OF THE ART

In the field of livestock breeding, insemination is an important step to optimise herd management. This step is all the more crucial as it helps to maximise the milk production periods, for example in the case dairy cows. For these reasons, the quality of the insemination and thus the semen used is essential.

In fact, an insemination that does not lead to a gestation of the animal has a negative impact on the profitability of a farm. For example, for a cow, a successful insemination is estimated by the absence of a return to oestrus recorded during a period of 90 days after the act of insemination. If unsuccessful, the annual milk production of the animal concerned is directly impacted downward. This induces a lower operating income for the farmer. In addition, it is necessary to repeat the operation of insemination. It is therefore important to reduce the uncertainties associated with this intervention.

Thus, the evaluation of the quality of a semen is a considerable challenge for analytical laboratories and semen producers.

This quality was first estimated according to animal selection protocols However, it has been found that an animal with a very good genetic makeup is not necessarily a good breeding stock. In addition, the quality of the semen of an animal selected for its good overall reproduction rate may vary according to the health of the animal during sampling.

We then tried to evaluate the quality of the collected semen. This quality has been evaluated from the semen as a whole and/or from its different components according to different criteria.

Semen is a complex biological fluid, consisting of the secretions of different organs of the reproductive tract, containing the male gametes. The semen consists among other substances of sperm, seminal plasma and exosomes.

Fertility, which is the ability to procreate, is a consensual term used to evaluate the quality of a semen. However, this term has the disadvantage of being general and vague. It is not satisfactory to perform discrimination of male individuals. Therefore and according to the needs, different criteria have been defined in order to evaluate the fertility of an individual.

These criteria include:
- the fertilisation rate, which is the fusion rate between the male and female gametes allowing the formation of the zygote;
- the NRR, acronym for non-return rate, is an estimate of the result of insemination ended with a success or a failure based on the absence of a return to oestrus recorded during an interval of X days after the act of insemination;
- the conception rate, which is the percentage of females diagnosed in pregnancy during an interval of X days after the act of insemination (DeJarnette J M, Amann R P. «Understanding estimates of AI sire fertility: From A to Z.» 23rd Technical Conference on Artificial Insemination & Reproduction, Milwaukee, Wis. 2010).

A difficulty is that a measurement of these criteria requires, to get a result, a longer or shorter waiting, depending on the animal species or breeds.

Many in vitro tests have thus been developed to assess the semen, some of which are recommended particularly in human clinical operations by the World Health Organization. «WHO laboratory manual for the examination and processing of human semen.» Geneva: World Health Organization; 2010). In humans as for other vertebrate species, existing tests are not satisfactory in predicting the fertility of a sperm sample analysed (De Jonge C. «Semen analysis: looking for an upgrade in class.» Fertil Steril 2012-97:260-266 and Kastelic J P, Thundathil J C. «Breeding soundness evaluation and semen analysis for predicting bull fertility.» Reprod Domest Anim Zuchthyg 2008; 43 Suppl 2:368-373). The macroscopic (volume, colour, viscosity . . . ) and microscopic (motility, concentration, morphology . . . ) tests currently performed routinely eliminate semens with extremely poor qualities, but are not conclusive to identify idiopathic infertility or hypofertile animals. Moreover, they do not allow, for example, to predict the variability of fertility in bulls observed in the field. This difficulty lies among others in the fact that spermatozoa are complex cells and that their evaluation has some difficulties (Mocé E, Graham J K. «In vitro evaluation of sperm quality.» Anim Reprod Sci 2008; 105:104-118).

One of the problems inherent in the assessment of the quality of a semen stems from the fact that the sample contains a heterogeneous population of spermatozoa. Further to their training during spermatogenesis, sperm flow through the epididymis and accumulate in the tail of this body until the moment of ejaculation (Dacheux J-L, Dacheux F. «New insights into epididymal function in relation to sperm maturation.» Reprod Camb Engl 2014; 147:R27-42). The spermatozoa thus stored stem from different waves of spermatogenesis, hence sperm from the same ejaculate have different degrees of maturation ensuring, in vivo, a wider window of fertilisation. In vivo, during their transit through the female reproductive tract, some spermatozoa are eliminated from the population. Conversely, in the in vitro analysis of a semen, the sample may include several infertile spermatozoa, which can be motionless, dead, malformed, . . . (Holt W V, Van Look K J W. «Concepts in sperm heterogeneity, sperm selection and sperm competition as biological foundations for laboratory tests of semen quality.» Reprod Camb Engl 2004; 127:527-535 et Rodríguez-Martínez H. «Can we increase the estimated value of semen assessment?» Reprod Domest Anim Zuchthyg 2006; 41 Suppl 2:2-10 et Petrunkina A M, Volker G, Brandt H, Töpfer-Petersen E, Waberski D. «Functional significance of responsiveness to capacitating conditions in boar spermatozoa.» Theriogenology 2005; 64:1766-1782). So infertile spermatozoa are evaluated as well as those who will be able to fertilize the egg.

Another problem inherent in the quality assessment of a semen is that the spermatozoa do not respond consistently to the same stress (Petrunkina A M, Volker G, Brandt H, Töpfer-Petersen E, Waberski D. «Functional significance of responsiveness to capacitating conditions in boar spermatozoa.» Theriogenology 2005; 64: 1766-1782), even if spermatozoa have similar characteristics to certain specific times. Finally, the complexity of working with spermatozoa also comes from the fact that this cell is multicompartmented and that each of these sub-compartments must be intact and functional to allow fertilisation (Amann R P, Hammerstedt R H. «In vitro evaluation of sperm quality: an opinion.» J Androl 1993; 14:397-406).

To ensure fertilization, the spermatozoa must have several features such as mobility, ATP production, induction of hyperactivation, a faculty to achieve their capacitation and their acrosome reaction, a functional plasma membrane, a capacity to recognise and bind to the zona pellucida, or, have an intact DNA, etc. Spermatozoa are therefore complex, multifunctional cells that require the proper functioning of several parameters to reach their ultimate goal: fertilisation and support of early embryonic development.

The infertility or subfertility of an individual may be the result of a multitude of changes.

Thus, a test evaluating one of the parameters of spermatozoa finds it difficult to detect a defective spermatozoa for a property other than that assessed by the test. A disadvantage of such a test is overestimated fertility of the sample (Graham J K, Mocé E. «Fertility evaluation of frozen/thawed semen.» Theriogenology 2005; 64:492-504). In addition, it is unlikely that this laboratory test evaluating a parameter of spermatozoa is able to detect the proportion of spermatozoa containing all the parameters necessary to fertilise the oocyte and ensure embryonic development.

That is why multiparameter testing proves interesting. Indeed, the analysis of several parameters of a spermatozoa sample achieves an overall view of the sample analysed and improves the detection of a defective parameter. In this way, the multiparametric analysis would better explain the fertility differences between bulls analysed (Januskauskas A, Johannisson A, Söderquist L, Rodriguez-Martinez H. «Assessment of sperm characteristics post-thaw and response to calcium ionophore in relation to fertility in Swedish dairy AI bulls.» Theriogenology 2000; 53:859-875).

Another part of the problem faced in assessing the fertility of an animal from laboratory results is associated with underlying problems at the laboratory analysis itself. To be valid, a laboratory test should be objective (create little error due to human judgment or bias), repeatable (produce the same results during the repeat of the test), accurate (accurately assess a parameter of sperm), fast and inexpensive (Graham J K. «Assessment of sperm quality: a flow cytometric approach.» Anim Reprod Sci 2001; 68:239-247). Currently, few laboratory tests for semen analysis have all these characteristics.

In recent years, the use of the CASA analysis technique (acronym for Computer Assisted Sperm Analysis) and flow cytometry analysis allowed an evolution of methods of quality assessment of semen in laboratories.

A disadvantage of these multiparameter analysis techniques is that they do not allow for in vitro measurement which is predictive of in vivo fertility. This lack of conclusive results can be attributed to the parameters and markers used for these tests, which are too weakly correlated with the phenotype to be predicted and/or are redundant and/or are limited in number.

High-throughput approaches grouped under the term "omics" or "Phenomics" allow more thorough assessments of the semen quality with interesting prospects in human clinical studies (Egea R R, Puchalt N G, Escrivá MM, Varghese A C. OMICS: «Current and future perspectives in reproductive medicine and technology.» J Hum Reprod Sci 2014; 7:73-92) as well as agronomy (Robert C. «Challenges of functional genomics applied to farm animal gametes and pre-hatching embryos.» Theriogenology 2008; 70:1277-1287).

A disadvantage for the routine use of these known techniques results from their costs.

Another disadvantage is the complexity of implementation of these techniques.

Yet another disadvantage is that these known techniques are made from a fraction of a sample and not from an intact sample.

Other techniques have been proposed to enable the analysis of intact cells, including determining their lipidome (Jones J J, Stump M J, Fleming R C, Lay J O, Wilkins C L. «Strategies and data analysis techniques for lipid and phospholipid chemistry elucidation by intact cell MALDI-FTMS.» J Am Soc Mass Spectrom 2004; 15:1665-1674) or their proteome (Labas V, Spina L, Belleannee C, Teixeira-Gomes A-P, Gargaros A, Dacheux F, Dacheux J-L. «Analysis of epididymal sperm maturation by MALDI profiling and top-down mass spectrometry.» J Proteomics 2015; 113:226-243).

A disadvantage of these intact cell analysis techniques is that they do not allow characterisation of intact spermatozoa for a set of molecular and/or structural characters simultaneously.

Also known is a technique for analysing the quality of a semen by infrared spectroscopy, which particularly involves analysing an irradiated sample under radiation in the mid-infrared (the radiation wavelength ranges between 2.5 µm and 25 µm), also known by the MIR acronym.

When a biological sample is irradiated by MIR beam, the radiation will be partially and selectively absorbed depending on the chemical bonds of the different molecules present in the sample. An infrared spectrum is therefore composed of absorption bands that can be attributed to specific chemical groups. The position of the bands depends both on the nature of the bond, but also on its environment. Thus, the position of the absorption band makes it possible to connect these absorption bands to particular molecules such as proteins, lipids or carbohydrates.

Studies were conducted to evaluate the performance of the spectroscopic technique in the mid-infrared for various applications. We can for example quote a study aimed at bacterial typing (Helm D, Labischinski H, Schallehn G, Naumann D. «Classification and identification of bacteria by Fourier-transform infrared spectroscopy.» J Gen Microbiol 1991; 137:69-79; et Stamm I, Hailer M, Depner B, Kopp P A, Rau J. «*Yersinia enterocolitica* in diagnostic fecal samples from European dogs and cats: identification by fourier transform infrared spectroscopy and matrix-assisted laser desorption ionization-time of flight mass spectrometry.» J Clin Microbiol 2013; 51:887-893), a study on the identification of pathologies such as cancer (Backhaus J, Mueller R, Formanski N, Szlama N, Meerpohl H-G, Eidt M, Bugert P. «Diagnosis of breast cancer with infrared spectroscopy from serum samples.» Vib Spectrosc 2010; 52:173-177; et Kallenbach-Thieltges A, Großerüschkamp F, Mosig A, Diem M, Tannapfel A, Gerwert K. «Immunohistochemistry, histopathology and infrared spectral histopathology of colon cancer tissue sections.» J Biophotonics 2013; 6:88-100; et Lewis P D, Lewis K E, Ghosal R, Bayliss S, Lloyd A J, Wills J, Godfrey R, Kloer P, Mur L A J. «Evaluation of FTIR spectroscopy as a diagnostic tool for lung cancer using sputum.» BMC Cancer 2010; 10:640), or articular pathologies (Canvin J M G, Bernatsky S, Hitchon C A, Jackson M, Sowa M G, Mansfield J R, Eysel H H, Mantsch H H, El-Gabalawy H S. «Infrared spectroscopy: shedding light on synovitis in patients with rheumatoid arthritis.» Rheumatol Oxf Engl 2003; 42:76-82), or the detection of contaminants in the food industry (de Carvalho B M A, de Carvalho L M, Reis Coimbra J S dos, Minim L A, de Souza Barcellos E, da Silva Júnior W F, Detmann E, de Carvalho G G P. «Rapid detection of whey in milk powder samples by spectrophotometric and multivariate calibration.» Food Chem 2015; 174:1-7).

The Fiber Evanescent Wave Spectroscopy infrared analysis (FEWS) allows to work in the MIR. This analysis is based on the use of a sensor composed of fiber optic chalcogenide glass which is described, for example, in documents FR2958403, WO2013017324, and FR1450661. When a light wave propagates in an optical fiber, it does so by multiple reflections, all of these rays constituting the evanescent wave. This wave can then be absorbed by a medium in contact with the fiber.

This technique offers many advantages. In contrast to discrete analyses aimed at finding and/or quantifying certain metabolites defined a priori, the MIR analysis makes it possible to obtain an overall image of the metabolic profile of the sample in a single analysis, thus taking into account the interactions between molecules. The particularity of the fiber optic sensor makes it a tool that can be used in a liquid medium while being insensitive to the water content of the samples, unlike other acquisition techniques. The result is fast and does not require special treatment of samples.

Several uses of Raman spectroscopy have already shown insights into the potential of this technique applied to the field of reproduction (Mallidis C, Sanchez V, Wistuba J, Wuebbeling F, Burger M, Fallnich C, Schlatt S. «Raman microspectroscopy: shining a new light on reproductive medicine.» Hum Reprod Update 2014; 20:403-414). This technique has been applied to the evaluation of the integrity of spermatozoa DNA (Mallidis C, Wistuba J, Bleisteiner B, Damm O S, Gross P, Wübbeling F, Fallnich C, Burger M, Schlatt S. «In situ visualization of damaged DNA in human sperm by Raman microspectroscopy.» Hum Reprod Oxf Engl 2011; 26:1641-1649; et Mallidis C, Schlatt S, Wistuba J, Fallnich C, Gross P, Burger M, Wuebbeling F. «Means and methods for assessing sperm nuclear DNA structure.» WO2013064159 A1, 2013), to analysis of the acrosome for determining the fertilizing ability of spermatozoa (李铮, 朱勇, 刘锋, 何琳, 刘宇飞. «Sperm acrosome zone Raman spectrum peak and use thereof.» CN103698310 A, 2014) or plasma seminal analysis for diagnostic purposes (Huang Z, Chen X, Chen Y, Chen J, Dou M, Feng S, Zeng H, Chen R. «Raman spectroscopic characterization and differentiation of seminal plasma.» J Biomed Opt 2011; 16:110501-1105013).

However, it has never been used so far to characterise a complete sample of semen.

4. SUMMARY OF THE INVENTION

An aspect of the present disclosure relates to a method for determining of the quality of a semen of a vertebrate animal.

In the context of the invention, the term "animal" refers to its current meaning, namely a non-human heterotrophic living being. More specifically, the invention relates to a method of determining the quality of a semen of a non-human vertebrate. For example, they may be large animals, small livestock, an avian or a fish.

This method for determining the quality of a semen of a vertebrate animal comprises the following steps:
  measuring at least one absorption spectrum of a sample of said semen;
  selecting a number n, with ≥4, of wave numbers $\sigma_{j\,(j\in[1;n])}$ which are characteristic of the semens of the breed or of the species of said animal;
  determining from said absorption spectrum or spectra of a value of the absorption $X_j$ and/or of a value of the second derivative of the absorption $X_j''{}_{(j\in[1;n])}$ for each of said n wave numbers $\sigma_{j\,(j\in[1;n])}$;
  calculating a non-return rate Y at a predefined number of days from said absorption values $X_j$ and/or the second derivative of the absorption $X_j''$ previously determined.

Thus, in an unprecedented manner, the invention proposes to use the absorption spectrum of a semen to evaluate the quality of an animal's semen, from a reduced number of wave numbers representative of explanatory variables, which are characteristic of semens of the breed or of the species of animal.

The invention makes it possible in particular to determine a non-return rate (NRR), for example a non-return rate in heat at 22, 28, 30, 56, 90 or 120 days, for 98% of the semens of a breed or an animal species with an accuracy of ±10 points, from only 20 explanatory variables and with an accuracy of ±5 points for 86% of semens. It should be borne in mind that the NRR at D days (NRRD) is an estimate of the result of insemination, with a success or a failure, based on the absence of a return to oestrus recorded during an interval of D days after the act of insemination. After D days, cows not returning to oestrus are considered pregnant.

It should also be noted that the invention allows to evaluate the quality of the semens of all the breeds or species of vertebrate animals, without exception, quickly and cheaply.

In the context of the invention, the term animal breed, within the same animal species, a population of homozygous individuals for a certain number of characters conditioning a set of traits or morphological features and the same general trend of aptitudes within the same animal species, such as, for example, a bovine breed, an equine breed, a porcine breed, a sheep breed, a goat breed, a duck breed, a chicken breed, a goose breed, a turkey breed, a rabbit breed.

According to one particular aspect of the invention, said non-return rate Y is calculated according to the mathematical law $$Y = \beta_0 + \sum_{j=1}^{n} \beta_j X_j''$$

where $X_j''{}_{(j\in[1;n])}$ is the normalized second derivative of the absorption for the wave number $\sigma_j$ and the weighting coefficients $\beta_0$ et $\beta_j{}_{(j\in[1;n])}$ are constants.

The non-return rate is thus calculated deterministically.

Preferably, the values of said weighting coefficients are obtained from processing the absorption spectra measurements of a plurality of semen samples of a reference vertebrate population, the non-return rates of which are known.

According to an advantageous embodiment of the invention, during said measuring step, at least 2, preferably at least 3 absorption spectra of a sample of said semen are measured and said step of determining values of the absorption and/or second derivatives of the absorption comprises a step of performing an average of said measured spectra from which said values of absorption and/or second derivatives of absorption are determined.

This reduces the sensitivity to measurement artefacts and to disturbances.

Advantageously, the number n of wave numbers $\sigma_j$ $_{(j \in [1;n])}$ is greater than or equal to 7, preferably greater than or equal to 9, even more preferably greater than or equal to 13, still more preferably greater than or equal to 20.

The accuracy of semen quality determination is increased by taking into account a larger but limited number of wave numbers. The invention is not limited to wave numbers greater than or equal to 4. The number n of wave numbers $\sigma_j$ $_{(j \in [1;n])}$ can be equal to 2 or 3 without departing from the scope of the invention.

In a preferred aspect of the invention, said wave numbers are each representative of a molecule or set of molecules selected from the group consisting of at least: lipids, carbohydrates, proteins, nucleic acids, or a combination of a lipid, carbohydrate, protein, or nucleic acid molecule with at least one other lipid, carbohydrate, protein, or nucleic acid molecule. For example, for a bull, we can choose from about 600 explanatory variables.

In a particular embodiment of the invention, said vertebrate is a bull and the non-return rate is a 90-day non-return rate, said bull coming from a breed selected from the group comprising at least one of the following breeds: Abondance, Béarnaise, Bordelaise, Bretonne pie noir, Brune, Froment du Léon, Jersiaise, Montbéliarde, Pie rouge des plaines, Prim'Holstein, Rouge flamande, Bleue du nord, Normande, Salers, Tarentaise.

Preferably, at least one of said wave numbers $\sigma_j$ $_{(j \in [1;n])}$ is selected from the range of wave number [960 cm$^{-1}$; 1100 cm$^{-1}$], [1440 cm$^{-1}$; 1550 cm$^{-1}$] or [2800 cm$^{-1}$; 3200 cm$^{-1}$] or in the amid band B.

According to a particular aspect of the invention, said wave numbers $\sigma_j$ $_{(j \in [1;n])}$ are selected from the group consisting of at least 955.0±0.1 cm$^{-1}$, 963.1±0.1 cm$^{-1}$, 1012.1±0.1 cm$^{-1}$, 1036.6±0.1 cm$^{-1}$, 1095.8±0.1 cm$^{-1}$, 1124.3±0.1 cm$^{-1}$, 1136.6±0.1 cm$^{-1}$, 1365.1±0.1 cm$^{-1}$, 1383.5±0.1 cm$^{-1}$, 1428.4±0.1 cm$^{-1}$, 1444.7±0.1 cm$^{-1}$, 1452.9±0.1 cm$^{-1}$, 1503.9±0.1 cm$^{-1}$, 1520.2±0.1 cm$^{-1}$, 2805.7±0.1 cm$^{-1}$, 2956.7±0.1 cm$^{-1}$, 2969.0±0.1 cm$^{-1}$, 2987.4±0.1 cm$^{-1}$, 3089.4±0.1 cm$^{-1}$, 3091.4±0.1 cm$^{-1}$.

In a particular embodiment of the invention, said wave numbers $\sigma_j$ $_{(j \in [1;n])}$ are selected from the group consisting of at least 3165±1 cm$^{-1}$, 3136±1 cm$^{-1}$, 3103±1 cm$^{-1}$, 3071±1 cm$^{-1}$, 3026±1 cm$^{-1}$, 2977±1 cm$^{-1}$, 2975±1 cm$^{-1}$, 1736±1 cm$^{-1}$, 1689±1 cm$^{-1}$, 1661±1 cm$^{-1}$, 1618±1 cm$^{-1}$, 1514±1 cm$^{-1}$, 1448±1 cm$^{-1}$, 1430±1 cm$^{-1}$, 1344±1 cm$^{-1}$, 1338±1 cm$^{-1}$, 1336±1 cm$^{-1}$, 1316±1 cm$^{-1}$, 1214±1 cm$^{-1}$, 1183±1 cm$^{-1}$, 1103±1 cm$^{-1}$, 1099±1 cm$^{-1}$, 1020±1 cm$^{-1}$, 975±1 cm$^{-1}$.

In a particular embodiment of the invention, the number n of said selected wave numbers $\sigma_j$ $_{(j \in [1;n])}$ is thirteen and the values of said thirteen selected wave numbers $\sigma_j$ $_{(j \in [1;n])}$ are: 3165±1 cm$^{-1}$, 3136±1 cm$^{-1}$, 3103±1 cm$^{-1}$, 2975±1 cm$^{-1}$, 1736±1 cm$^{-1}$, 1661±1 cm$^{-1}$, 1515±1 cm$^{-1}$, 1448±1 cm$^{-1}$, 1430±1 cm$^{-1}$, 1316±1 cm$^{-1}$, 1214±1 cm$^{-1}$, 1020±1 cm$^{-1}$, 975±1 cm$^{-1}$.

In a particular embodiment of the invention, the number n of said selected wave numbers $\sigma_j$ $_{(j \in [1;n])}$ is fifteen and in that the values of said fifteen selected wave numbers $\sigma_j$ $_{(j \in [1;n])}$ are: 3071±1 cm$^{-1}$, 3026±1 cm$^{-1}$, 2977±1 cm$^{-1}$, 1689±1 cm$^{-1}$, 1618±1 cm$^{-1}$, 1515±1 cm$^{-1}$, 1430±1 cm$^{-1}$, 1344±1 cm$^{-1}$, 1338±1 cm$^{-1}$, 1336±1 cm$^{-1}$, 1183±1 cm$^{-1}$, 1103±1 cm$^{-1}$, 1099±1 cm$^{-1}$, 1020±1 cm$^{-1}$, 975±1 cm$^{-1}$.

Preferably, said step of measuring at least one absorption spectrum comprises a step of preparing said sample from said semen.

In a particular embodiment of the invention, the method for determining the quality of a semen as described above comprises a step of comparing said non-return rate Y with a predetermined threshold, making it possible to select said semen for reproduction purposes in the case where said non-return rate Y is greater than or equal to said predetermined threshold.

The result is an effective technique, particularly easy to implement for selecting quality semens.

In an advantageous embodiment of the invention, said threshold is greater than or equal to 0.4, preferably greater than or equal to 0.5, even more preferably greater than or equal to 0.6.

5. LIST OF FIGURES

Other features and advantages of the invention will become evident on reading the following description of one particular embodiment of the invention, given by way of illustrative and non-limiting example only, and with the appended drawings among which.

6. DETAILED DESCRIPTION OF THE INVENTION

6.1. Experimental Protocol

The samples analysed are bovine ejaculates in the form of straws, preserved in liquid nitrogen. Preliminary analyses were performed on 130 ejaculates from 50 different bulls from the Prim'Holstein breed. The NRR90 gross indicator was used to qualify the quality of ejaculates.

6.1.1. Sample Preparation

During the sample preparation stage, in a first step, straws are thawed in a water bath at 37° C. for 30 seconds. In a second step, the straws are analysed. For this, the contents of the straws are placed in a 1.5 ml Eppendorf tube. Seven microliters are then deposited on the sensor for MIR spectral acquisition of a "straw". In a third step, a supernatant is extracted by centrifugation at 3500 g for 5 min at 15° C. The supernatant is then deposited on the sensor for the acquisition of the "supernatant" spectrum. In a fourth step, the pellet is rinsed with 600 µl of 0.9% NaCl and centrifugation is then performed. The pellet is again suspended in 3.5 µl of 0.9% NaCl and deposited on the sensor for the acquisition of the "pellet" spectrum.

6.1.2. MIR Spectral Acquisition of a Straw

The spectra are acquired in absorbance from 4000 to 400 cm$^{-1}$. The spectral resolution is set at 4 cm$^{-1}$, with a zero-filling factor of 2, and 64 scans are recorded.

A sensor is placed in the spectrometer, the baseline is recorded to calibrate the device, then 7 µl of sample is deposited on the sensor. The spectrum is recorded after 6 minutes.

6.1.3. Spectrum Processing

The spectra are analysed in the 3800-940 cm$^{-1}$ domain, the absorption domain of the majority of biomolecules. A straight line is generated from 2800 to 1800 cm$^{-1}$ to eliminate the contribution of $CO_2$, then the second derivative (Savisky-Golay algorithm with 13 smoothing points) is calculated from 3200 to 2800 cm$^{-1}$ and 1800 to 940 cm$^{-1}$. Then a vector normalisation of the second derivatives is carried out. Quality criteria are defined to reject nonconforming spectra.

6.1.4. Choice of the Matrix for the Prediction of the Quality of the Semen

Figure 2:
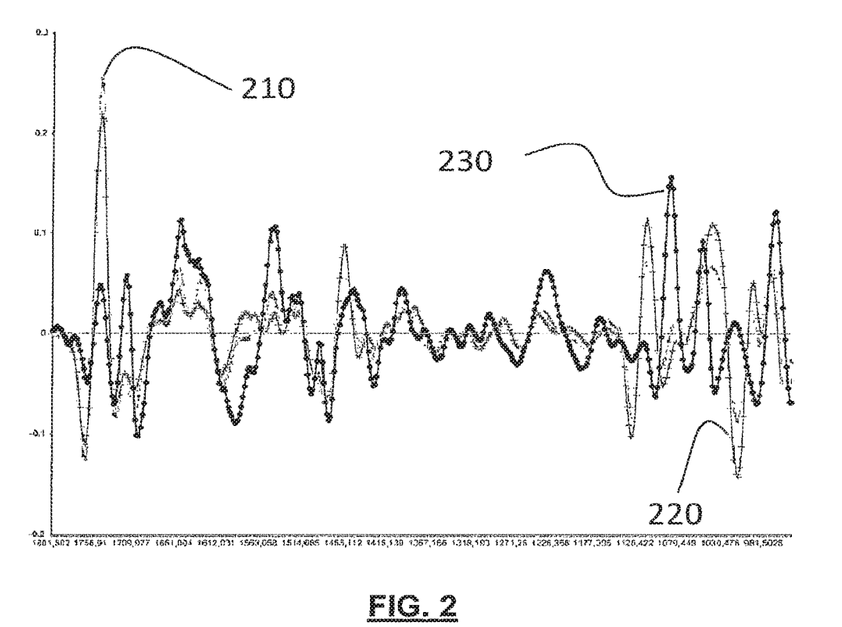
FIG. 2 represents MIR, derived and standardised spectra acquired from a straw, a supernatant and a pellet.
Figure 3:
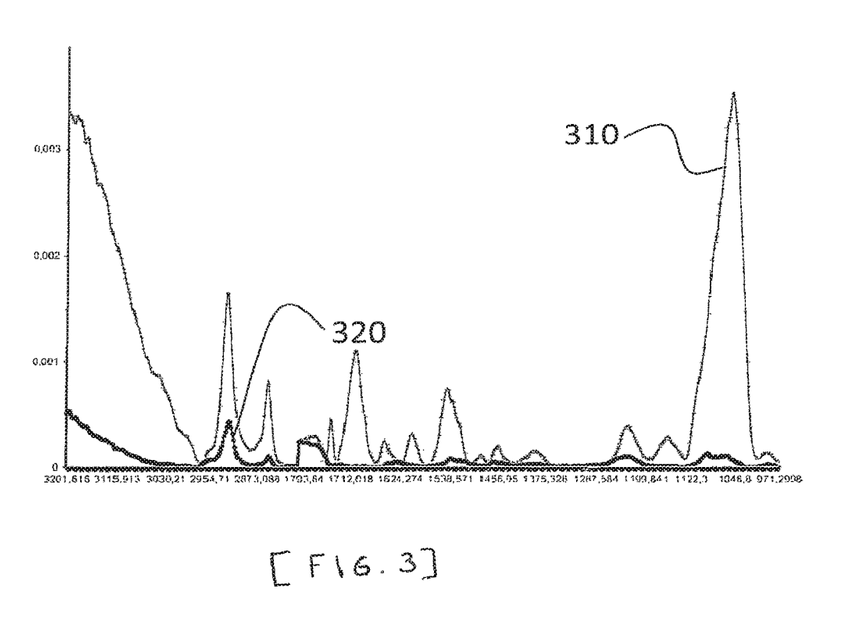
FIG. 3 is a representation of the variance of a straw and of a pellet from the same ejaculate depending on the wave number.

Three types of acquisitions were made and compared: ejaculate or total semen, pellet and supernatant (centrifugation of the semen). An observation of the spectra (see FIG. 2) highlights that the spectra of "straw" 210 and "supernatant" 220 have many similarities. Principal Component Analysis (PCA) is performed on the data in order to compare the spectra. It appears on the factorial map that the spectra acquired from the supernatant are very close to those acquired from the total ejaculate. Thus the spectra acquired from the straws contain a biochemical information very close to that of the seminal fluid. Or, the latter is strongly diluted (from 3 to 30 times) in a buffer before freezing and is therefore not determinant of the specific quality of the diluted/frozen/thawed semen of the bull since all the ejaculates are treated in the same way. Due to the greater or lesser dilution of the ejaculate, the MIR spectra of the straws necessarily reflect the biochemical composition of the dilution medium. This contribution to the MIR spectra may therefore mask that of the spermatozoa that are supposed to contain the spectral information that makes the difference from the point of view of fertility. Moreover, if a defect of fertility linked only to a lower quality of the seminal fluid (fructose, pH, . . . ) is considered, it is expected that this defect is offset by the dilution in the buffer medium. It turns out that the spectral information that makes the difference is to be found on the cells alone, rather than on the more or less diluted overall sample. The variability of the measurements between straw and pellet 230 was also taken into account. For this, the variances were calculated on the 3 spectra acquired for the same ejaculate. The raw spectra, that is the non-derivative spectra, were first standardised by the Multiplicative Scatter Correction MSC method in order to overcome the baseline variations. As shown in FIG. 3, with a representation of the variance as a function of wave number (in cm$^{-1}$) for a discussion of the straws 310 and the pellet 320, it appears generally that the signals acquired from the total semen have more variability especially in the range of 1000-940 cm$^{-1}$.

The measurements are therefore carried out on the centrifugation pellet essentially containing the spermatozoa.

6.2. Construction of Models of Determining the Quality of a Semen

6.2.1. Reference Samples

Eighty-six ejaculates, from 40 Holstein bulls, the 90-day gross non-return rate, or NRR90 gross is known, were used for the establishment of the law or equation to determine the quality of the ejaculate.

These ejaculates come from bulls aged 11 months to 10.5 years at the time of collection of their ejaculates. The distribution of the number of ejaculates per bull is as follows: 8, 18 and 14 bulls respectively produced 1, 2 or 3 ejaculates.

6.2.2. Preparation of Straws:

For each ejaculate, six straws are thawed by placing them in a water bath at 37° C. for 30 seconds.

The contents of six straws are emptied into an Eppendorf tube 1.5 ml, then it undergoes a centrifugation at 3500 g for 5 min at 15° C. The supernatant is removed and the pellet is rinsed with 600 µl of 0.9% NaCl. This step is renewed once. Following the second rinsing, a new centrifugation is applied and the pellet is again suspended in 10 µl of 0.9% NaCl.

6.2.3. Acquisition of Spectra

From this preparation, three spectra are acquired for each ejaculate. The acquisition of each of the spectra is carried out with a pitch of 2 cm$^{-1}$, on a spectrometer whose precision, whatever the position, that is to say the wave number, is 0.1 cm$^{-1}$.

To acquire each of the spectra, 7 µl of the suspension formed of the pellet and the saline solution are deposited in the sensor. The spermatozoa are irradiated in the midinfrared and their absorption spectrum is recorded after 6 minutes.

6.2.4. Data Analysis

The spectra are subject to quality control on various criteria before being selected for further analysis. Criteria considered for quality control include signal strength, interference, signal-to-noise ratio, and water content.

The average of three spectra acquired is performed to obtain an averaged spectrum of the ejaculate.

The averaged spectrum is processed according to the procedure previously described in paragraph 6.1.3.

For all the samples, the spectra are divided into two categories, the calibration spectra from the analysis of 70 ejaculates and the validation spectra from the analysis of the remaining eighteen ejaculates. Calibration spectra are used to construct the model in order to relate a variable to explain, here the NRR90 gross, and explanatory variables that is to say an optimised selection of wave numbers of the spectrum. Once the model has been optimised, the validation spectra are used to evaluate the predictive performance of the model.

The reduction of explanatory variables is performed by a genetic algorithm associated with a 10% cross-validation R-PLS. Once this reduction completed, the choice of variables is optimised by repeating 100 linear regressions (LRs), with a cross-validation on 10% of the initial population. A validation of the explanatory variables accepted is made by integrating them into the law or the linear equation for predicting "unknown" samples.

6.2.5. Construction of Models of Determining the Quality of a Semen

The reference samples are split into a calibration subpopulation and a validation subpopulation. The learning process is carried out on ⅘th of the ejaculates, the validation on the 5th remaining and for each of the sub-populations, one maximises the number of ejaculates from different bulls while having a proportional representativity of the individuals in 3 classes of NRR90 defined as follows: NRR90<40%, 40%≤NRR90≤50% and NRR90>50%.

6.2.5.1. Mathematical Model

The mathematical model used is defined by the formula $$Y = \beta_0 + \Sigma_{j=1}^{n} \beta_j X_j'',$$

wherein:
Y is the NRR90 calculated for the ejaculate;
n (n≥4) is the number of wave numbers $\sigma_j$ considered in the model;
$X_j''$ is the normalised second derivative of the value of the absorption to the wavenumbers $\sigma_j$;
$\beta_0$ is the offset at the origin;
$\beta_j$ (1≤j≤n) is the weighting coefficient of the value of the normalised second derivative of the absorption $X_j''$, delineated by its standard error.

6.2.5.2. Examples of Models

Five models are constructed from respectively 7, 9, 13, 15 and 20 wave numbers, minimising the prediction error, RMSEP ("Root-Mean-Square Error of Prediction").

The spectral ranges of wavenumbers selected relate in particular the field of absorption of lipids 3200-2800 cm$^{-1}$, proteins (amide B band and domain 1440-1500 cm$^{-1}$) as well as DNA (1514 cm$^{-1}$, 1099 cm$^{-1}$ and 975 cm$^{-1}$).

a) 7 Wave Number Model

This model is detailed in Table 1, below. it has a calculated coefficient of determination R$^2$ (or "Multiple R-Squared") of 0.4804 and a RMSEP of 4.8%.

TABLE 1

| Explanatory variable j | Wave number σ (cm−1) | Coefficient βj Estimate | Standard error Std. Error | Test result t value | Probability Pr (>\|t\|) |
|---|---|---|---|---|---|
| 0 |  | 0.2277 | 0.2503 | 0.910 | 0.365812 |
| 1 | 2956.7 | 9.3246 | 2.4387 | 3.824 | 0.000263 |
| 2 | 1428.4 | −10.4157 | 4.4484 | −2.341 | 0.021764 |
| 3 | 1383.5 | −15.7746 | 5.2130 | −3.026 | 0.003356 |
| 4 | 1365.1 | 19.7086 | 5.7690 | 3.416 | 0.001011 |
| 5 | 1095.8 | −6.8730 | 1.4857 | −4.626 | 1.46e−05 |
| 6 | 1036.6 | 7.7556 | 2.3304 | 3.328 | 0.001337 |
| 7 | 963.1 | 3.7342 | 1.1538 | 3.236 | 0.001777 |

Distribution of residues, in minimum, maximum and quartiles:

| Minimum | 1$^{st}$ quartile | Median | 3$^{rd}$ quartile | Maximum |
|---|---|---|---|---|
| −0.144853 | −0.028759 | 0.000373 | 0.033174 | 0.109250 |

Residual standard error: 0.05298 with 78-degree freedom
Adjusted R-Squared: 0.4337
F-value or F-value of Fisher's test: 10.3 over 78-degree freedom, P-value (P-value of Fisher's test): 4.455e-09 a) 9 Wave Number Model

This 9 wave number model is detailed in Table 2, below. It has a calculated Multiple R-Squared of 0.5884 and a RMSEP of 4.49%.

TABLE 2

| Explanatory variable j | Wave number σ (cm−1) | Coefficient β Estimate | Standard error Std. Error | Test result t value | Probability Pr (>\|t\|) |
|---|---|---|---|---|---|
| 0 |  | −0.06038 | 0.30929 | −0.195 | 0.84573 |
| 1 | 2956.7 | 13.30697 | 2.44983 | 5.432 | 6.46e−07 |
| 2 | 1503.9 | −7.95636 | 2.95590 | −2.692 | 0.00874 |
| 3 | 1444.7 | 7.51796 | 3.27999 | 2.292 | 0.02467 |
| 4 | 1428.4 | −5.34138 | 4.70264 | −1.136 | 0.25960 |
| 5 | 1383.5 | −11.74606 | 4.99481 | −2.352 | 0.02128 |
| 6 | 1365.1 | 22.37749 | 5.23880 | 4.271 | 5.56e−05 |
| 7 | 1095.8 | −8.07636 | 1.48922 | −5.423 | 6.68e−07 |
| 8 | 1036.6 | 9.59107 | 2.14903 | 4.463 | 2.76e−05 |
| 9 | 963.1 | 3.14150 | 1.14317 | 2.748 | 0.00748 |

Distribution of residues in minimum, maximum and quartiles:

| Minimum | 1$^{st}$ quartile | Median | 3$^{rd}$ quartile | Maximum |
|---|---|---|---|---|
| −0.115369 | −0.023260 | −0.005633 | 0.021377 | 0.122507 |

Residual standard error: 0.04777 with 76-degree freedom
Adjusted Multiple R-Squared: 0.5397
F-value: 12.07 over 76-degree freedom, P-value: 1.325e-11 a) 13 Wave Number Model

This model is detailed in Table 3, below. It has a Multiple R-Squared of 0.2972 and a RMSEP of 6.3%.

TABLE 3

| Explanatory variable j | Wave number σ (cm$^{-1}$) | Coefficient β Estimate | Standard error Std. Error | Test result t value | Probability Pr (>\|t\|) |
|---|---|---|---|---|---|
| 0 |  | −0.1649 | 0.2345 | −0.703 | 0.48275 |
| 1 | 3164.886 | −1.2917 | 3.4928 | −0.370 | 0.71191 |
| 2 | 3136.318 | 3.9653 | 4.0591 | 0.977 | 0.32979 |
| 3 | 3103.67 | −1.8260 | 4.33 | −0.422 | 0.67368 |
| 4 | 2975.115 | −6.4489 | 3.4555 | −1.866 | 0.06346 |
| 5 | 1736.504 | 3.5545 | 1.5065 | 2.359 | 0.01926 |
| 6 | 1661.004 | 0.244 | 1.339 | 0.182 | 0.85558 |
| 7 | 1514.085 | −13.7841 | 2.3808 | −5.790 | 2.68e−08 |
| 8 | 1448.787 | 5.1977 | 1.584 | 3.281 | 0.00122 |
| 9 | 1430.422 | −23.5023 | 3.9896 | −5.891 | 1.59e−08 |
| 10 | 1316.152 | 6.6227 | 3.62 | 1.829 | 0.06881 |
| 11 | 1214.124 | 6.0439 | 3.0219 | 2 | 0.04684 |
| 12 | 1020.273 | −10.1756 | 2.5485 | −3.993 | 9.16e−05 |
| 13 | 975.3806 | −6.2081 | 1.4327 | −4.333 | 2.32e−05 |

Distribution of residues, in minimum. maximum and quartiles:

| Minimum | 1$^{st}$ quartile | Median | 3$^{erd}$ quartile | Maximum |
|---|---|---|---|---|
| −0.193993 | −0.033218 | 0.001113 | 0.039355 | 0.189818 |

Residual standard error: 0.06529 with 201-degree freedom
Adjusted R-Squared: 0.2517
F-value or F-value of Fisher's test): 6.537 over 13 and 201-degree of freedom, P-value (P-value of Fisher's test): 2.492e-10 a) 15 Wave Number Model

This model is detailed in Table 4, below. It has a Multiple R-Squared of 0.3861 and a RMSEP of 5.9%.

TABLE 4

| Explanatory variable j | Wave number σ (cm$^{-1}$) | Coefficient β Estimate | Standard error Std. Error | Test result t value | Probability Pr (>|t|) |
|---|---|---|---|---|---|
| 0 | | 0.1618 | 0.2033 | 0.796 | 0.427213 |
| 1 | 3071.021 | 12.198 | 4.3248 | 2.82 | 0.005281 |
| 2 | 3026.129 | 3.2041 | 3.8144 | 0.84 | 0.401918 |
| 3 | 2977.156 | −6.9854 | 3.4328 | −2.035 | 0.043185 |
| 4 | 1689.572 | 1.1852 | 0.7567 | 1.566 | 0.11887 |
| 5 | 1618.152 | −4.0715 | 1.5196 | −2.679 | 0.007995 |
| 6 | 1514.085 | −8.8803 | 2.4751 | −3.588 | 0.00042 |
| 7 | 1430.422 | −21.7955 | 3.7797 | −5.767 | 3.05e−08 |
| 8 | 1344.719 | −18.6905 | 6.149 | −3.040 | 0.002687 |
| 9 | 1338.598 | 38.3873 | 14.814 | 2.591 | 0.01027 |
| 10 | 1336.557 | −29.9668 | 13.9565 | −2.147 | 0.032991 |
| 11 | 1183.516 | 9.7122 | 3.5233 | 2.757 | 0.006384 |
| 12 | 1103.935 | 9.9713 | 2.9172 | 3.418 | 0.000765 |
| 13 | 1099.854 | −9.4505 | 2.0387 | −4.636 | 6.43e−06 |
| 14 | 1020.273 | −8.8229 | 2.4303 | −3.630 | 0.00036 |
| 15 | 975.3806 | −2.7333 | 1.3692 | −1.996 | 0.047276 |

Distribution of residues, in minimum, maximum and Quartiles:

| Minimum | 1$^{st}$ quartile | Median | 3$^{rd}$ quartile | Maximum |
|---|---|---|---|---|
| −0.178825 | −0.031587 | 0.001598 | 0.036951 | 0.163905 |

Residual standard error: 0.06133 with 199-degree freedom

Adjusted R-Squared: 0.3398

F-value or F-value of Fisher's test): 8.343 over 15 and 199-degree of freedom,

P-value (P-value of Fisher's test): 1.246e−14 a) 20 Wave Number Model

This 20 wave number model is detailed in Table 5, below. It has a calculated Multiple R-Squared of 0.7785 and a RMSEP of 3.29%.

TABLE 5

| Explanatory variable j | Wave number σ (cm-1) | Coefficient β Estimate | Standard error Std. Error | Test result t value | Probability Pr (>|t|) |
|---|---|---|---|---|---|
| 0 | | 0.2254 | 0.3695 | 0.610 | 0.544001 |
| 1 | 3091.4 | −24.6521 | 12.4717 | −1.977 | 0.052328 |
| 2 | 3089.4 | 16.4980 | 12.8488 | 1.284 | 0.203695 |
| 3 | 2987.4 | 10.5285 | 6.9744 | 1.510 | 0.135993 |
| 4 | 2969.0 | −7.9864 | 4.2662 | −1.872 | 0.065707 |
| 5 | 2956.7 | 9.7930 | 2.8089 | 3.486 | 0.000883 |
| 6 | 2805.7 | 17.1375 | 9.4481 | 1.814 | 0.074314 |
| 7 | 1520.2 | −4.1227 | 3.0247 | −1.363 | 0.177584 |
| 8 | 1503.9 | −4.8509 | 2.6843 | −1.807 | 0.075365 |
| 9 | 1452.9 | −0.8978 | 3.3514 | −0.268 | 0.789646 |
| 10 | 1444.7 | 7.9318 | 2.8937 | 2.741 | 0.007901 |
| 11 | 1428.4 | −15.6745 | 4.9713 | −3.153 | 0.002446 |
| 12 | 1383.5 | −15.7117 | 5.3184 | −2.954 | 0.004361 |
| 13 | 1365.1 | 12.0351 | 4.7273 | 2.546 | 0.013279 |
| 14 | 1136.6 | 6.2445 | 4.4486 | 1.404 | 0.165163 |
| 15 | 1124.3 | 0.4249 | 4.2978 | 0.099 | 0.921557 |
| 16 | 1095.8 | −7.5944 | 1.6238 | −4.677 | 1.52e−05 |
| 17 | 1036.6 | 6.1430 | 2.5989 | 2.364 | 0.021092 |
| 18 | 1012.1 | −3.9852 | 3.0611 | −1.302 | 0.197555 |
| 19 | 963.1 | 2.9781 | 1.3443 | 2.215 | 0.030237 |
| 20 | 955.0 | 4.0846 | 2.1981 | 1.858 | 0.067664 |

Distribution of residues in minimum, maximum and quartiles:

| Minimum | 1$^{st}$ quartile | Median | 3$^{rd}$ quartile | Maximum |
|---|---|---|---|---|
| −0.068317 | −0.024352 | −0.004114 | 0.019129 | 0.086793 |

Residual standard error: 0.03789 with 65-degree freedom

Adjusted Multiple R-Squared: 0.7104

F-value: 11.42 over 20 and 65-degree freedom, P-value: 2.375e−14

Figure 4A:
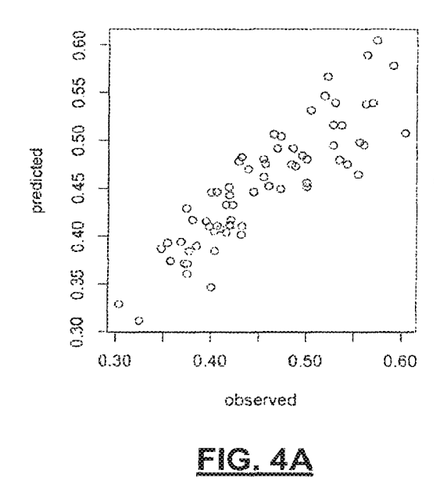
FIGS. 4A, 4B and 5 illustrate the correlation between NRR90 values calculated by a model with 20 wave numbers for ejaculate samples of Prim'Holstein bulls and known values for these same samples, respectively for 70 samples, for 16 samples and for all of these 86 samples.
Figure 4B:
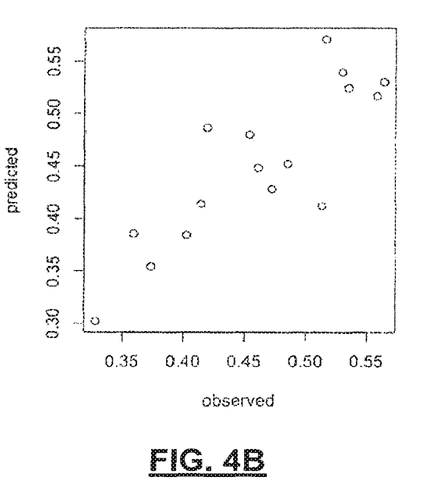
Figure 5:
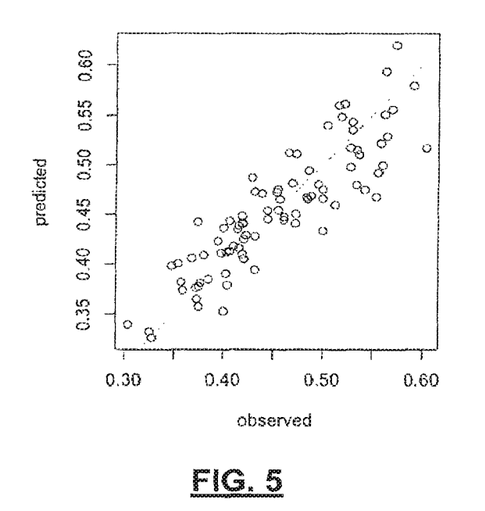

The relevance of this 20 wave number model is illustrated in FIGS. 4A, 4B and 5.

FIGS. 4A, 4B and 5 show the correlation between the NRR values predicted by the model and the values known for the samples used for the calibration (FIG. 4A), for the validation of the model (FIG. 4B) and for all the samples (FIG. 5).

Figure 6:
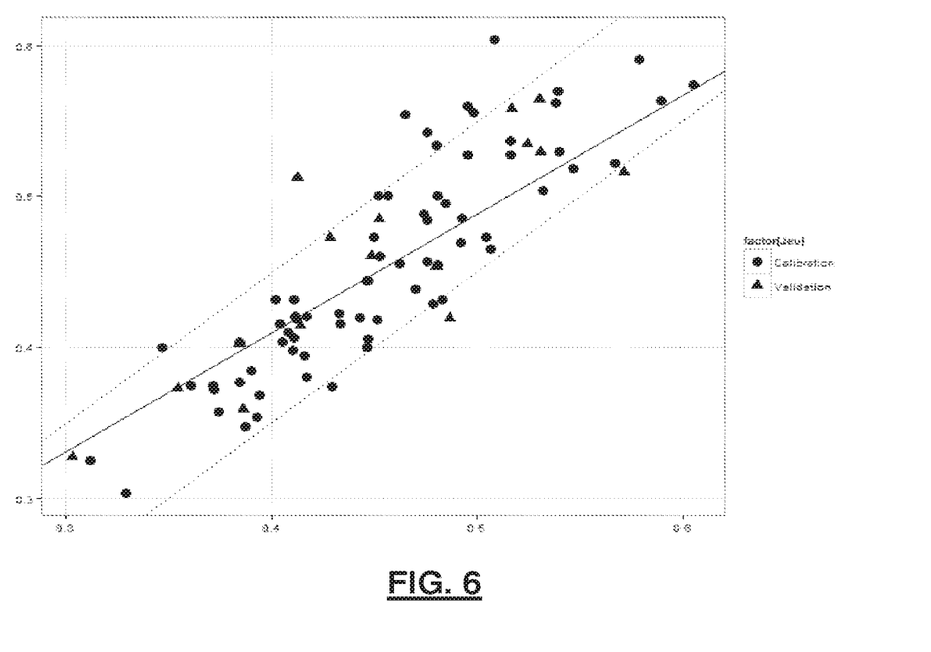
FIG. 6 is another representation of FIG. 5 in which two lines have been added, representing a difference in value of the NRR90 with respect to the model, respectively by +5 points and −5 points.

As can be seen in FIG. 6, for 86% of the samples, the model is accurate to less than 5 NRR points.

6.2 Exemplary Embodiment of the Invention

Figure 1:
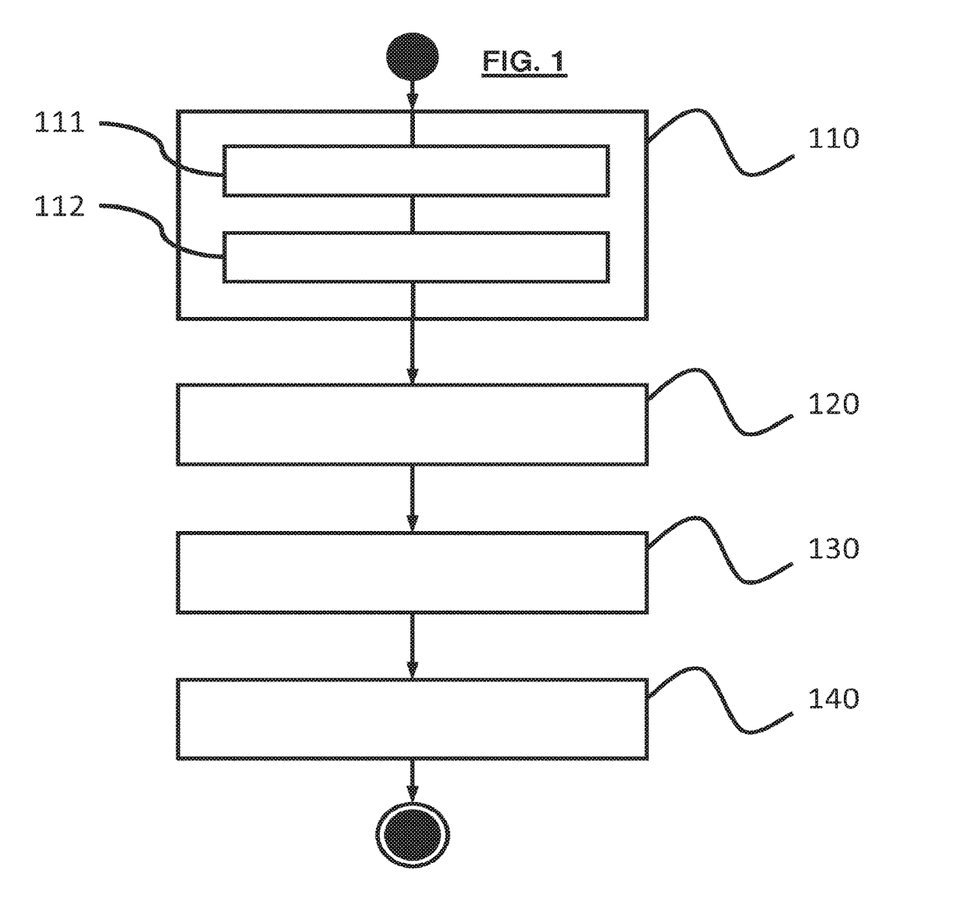
FIG. 1 illustrates, in block diagram form, the steps of an exemplary embodiment of a method for determining the quality of a semen of a bull according to the invention.

The steps of an exemplary embodiment of a method for determining the quality of a semen of a vertebrate animal of the invention, are illustrated with reference to FIG. 1, in diagrammatic form block.

At a step 110, we measure 3 times the spectrum of absorption of a prepared pellet, in a step 111, from two straws from a semen, with a Spectrometer model FT-IR SPID and with a sensor LS23 of DIAFIR (registered trademark).

In a variation of this particular embodiment of the invention, the absorption spectrum can be measured by transmission, by reflection or by ATR (Attenuated Total Reflection).

The 3 measured spectra are then averaged to obtain an averaged spectrum (step 112).

In a step 130, a value of the second derivative of the absorption $X_j''$ for n wave numbers $\sigma_j$ ($1 \leq j \leq n$) characteristic of the semens is determined from the averaged absorption spectrum of the breed of the animal, selected during a step 120.

Then, during a step 140, the 90-day non-return rate is calculated from the following mathematical law $$Y = \beta_0 + \Sigma_{j=1}^n \beta_j X_j''$$

where $\beta_0$ and $\beta_j$ ($1 \leq j \leq n$) are constants specific to the phenotype of the a breed of the animal which produces the semen, in using the values of the second derivatives of the absorption $X_j''_{(j \in [1;n])}$ determined at step 130.

In variations of this particular embodiment of the invention, it may be envisaged to calculate the 90-day non-return rate from the absorption values $X_j$ for n wave numbers $\sigma_j$ ($1 \leq j \leq n$) characteristic of the semens of the breed of the animal or using both values of the absorption and values of the second derivative of the absorption for the n numbers of waves $\sigma_j$ ($1 \leq j \leq n$) characteristic of the semens of the breed of the animal.

Although the invention has been described in connection with several particular embodiments, it is obvious that it is not limited thereto and that it comprises all the technical equivalents of the means described and their combinations if they are within the scope of the invention.

Thus, the method described in relation with an example applicable to all the breeds or the species of animal vertebrates by adapting the phenotype of the breed or species through the selection of wave numbers (explanatory variables) characteristic of the quality of the semen of the breed or species.

An exemplary embodiment of the invention remedies the shortcomings of the state of the art mentioned above.

Specifically, an exemplary embodiment of the invention provides a method for determining the quality of a semen of a vertebrate animal that is effective and reliable any type of semen.

An exemplary embodiment provides such a technique that is simple and rapid to implement.

An exemplary embodiment provides method for determining the quality of a semen of a vertebrate animal, with reduced cost price.

Although the present disclosure has been described with reference to one or more examples, workers skilled in the art will recognize that changes may be made in form and detail without departing from the scope of the disclosure and/or the appended claims.

The invention claimed is:

1. A method for determining the quality of a semen of a vertebrate animal, the method comprising:
   measuring at least one absorption spectrum of a sample of said semen with a spectrometer;
   selecting a number n, with n≥4, of wave numbers $\sigma_j$ $_{(j\in[1;n])}$ where the wave numbers are spatial frequencies in the spectrum characteristic of semen of a breed or of species of said animal;
   determining from said at least one absorption spectrum of at least one of a value of the absorption $X_j$ or a value of the second derivative of the absorption $X_j''$ $_{(j\in[1;n])}$ for each of said n wave numbers $\sigma_j$ $_{(j\in[1;n])}$; and
   calculating a non-return rate Y at a predefined number of days from at least one of said absorption values $X_j$ or the second derivative of the absorption $X_j''$ previously determined.

2. The method for determining the quality of a semen according to claim 1, wherein said non-return rate Y is calculated according to the mathematical law, wherein $X_j''$ $_{(j\in[1;n])}$ is the normalized second derivative of the absorption value for the wave number $\sigma_j$ and the weighting coefficients $\beta_0$ and $\beta_j$ $_{(j\in[1;n])}$ are constants.

3. The method for determining the quality of a semen according to claim 1, wherein the values of said weighting coefficients are obtained from a processing of measurements of the absorption spectra of a plurality of semen samples from a population of reference vertebrate, of which the non-return rates are known.

4. The method for determining the quality of a semen according to claim 1, wherein in said measuring, at least 2 absorption spectra of a sample of said seed are measured and said determining values of absorption or of second derivatives of the absorption comprises averaging said measured spectra from which said values of the absorption or the second derivatives of the absorption are determined.

5. The method for determining the quality of a semen according to claim 1, wherein the number n of wave numbers $\sigma_j$ $_{(j\in[1;n])}$ is greater than or equal to 7.

6. The method for determining the quality of a semen according to claim 1, wherein said wave numbers are each representative of a molecule or set of molecules selected from the group consisting of:
   lipids;
   carbohydrates;
   proteins;
   nucleic acids;
   a combination of a lipid, carbohydrate, protein, or nucleic acid molecule with at least one other lipid, carbohydrate, protein, or nucleic acid molecule.

7. The method for determining the quality of a semen according to claim 1, wherein said vertebrate is a bull and the non-return rate is a 90-day non-return rate, said bull coming from a breed selected from the group consisting of the following breeds: Abondance, Béarnaise, Bordelaise, Bretonne pie noir, Brune, Froment du Léon, Jersiaise, Montbéliarde, Pie rouge des plaines, Prim'Holstein, Rouge flamande, Bleue du nord, Normande, Salers, Tarentaise.

8. The method for determining the quality of a semen according to claim 1, wherein at least one of said wave numbers $\sigma_j$ $_{(j\in[1;n])}$ is selected in the wave number range [960 cm$^{-1}$; 1100 cm$^{-1}$], [1440 cm$^{-1}$; 1550 cm$^{-1}$] or [2800 cm$^{-1}$; 3200 cm$^{-1}$] or in the amide B band.

9. The method for determining the quality of a semen according to claim 1, wherein said wave numbers $\sigma_j$ $_{(j\in[1;n])}$ are selected from the group consisting of 3165±1 cm$^{-1}$, 3136±1 cm$^{-1}$, 3103±1 cm$^{-1}$, 3071±1 cm$^{-1}$, 3026±1 cm$^{-1}$, 2977±1 cm$^{-1}$, 2975±1 cm$^{-1}$, 1736±1 cm$^{-1}$, 1689±1 cm$^{-1}$, 1661±1 cm$^{-1}$, 1618±1 cm$^{-1}$, 1515±1 cm$^{-1}$, 1448±1 cm$^{-1}$, 1430±1 cm$^{-1}$, 1344±1 cm$^{-1}$, 1338±1 cm$^{-1}$, 1336±1 cm$^{-1}$, 1316±1 cm$^{-1}$, 1214±1 cm$^{-1}$, 1183 ±1 cm$^{-1}$, 1103±1 cm$^{-1}$, 1099±1 cm$^{-1}$, 1020±1 cm$^{-1}$, 975±1 cm$^{-1}$.

10. The method for determining the quality of a semen according to claim 9, wherein the number n of said selected wave numbers $\sigma_j$ $_{(j\in[1;n])}$ is equal to thirteen and the values of said thirteen selected wave numbers $\sigma_j$ $_{(j\in[1;n])}$ are: 3165±1 cm$^{-1}$, 3136±1cm$^{-1}$, 3103±1 cm$^{-1}$, 2975±1 cm$^{-1}$, 1736±1 cm$^{-1}$, 1661±1 cm$^{-1}$, 1515±1 cm$^{-1}$, 1448±1 cm$^{-1}$, 1430±1 cm$^{-1}$, 1316±1 cm$^{-1}$, 1214±1 cm$^{-1}$, 1020±1 cm$^{-1}$, 975±1 cm$^{-1}$.

11. The method for determining the quality of a semen according to claim 9, wherein the number n of said selected wave numbers $\sigma_j$ $_{(j\in[1;n])}$ is equal to fifteen and the values of said fifteen selected wave numbers $\sigma_j$ $_{(j\in[1;n])}$ are: 3071 ±1 cm$^{-1}$, 3026 ±1 cm$^1$, 2977 ±1 cm$^{-1}$, 1689 ±1 cm$^{-1}$, 1618 ±1 cm$^{-1}$, 1515 ±1 cm$^{-1}$, 1430 ±1 cm$^{-1}$, 1344 ±1 cm$^{-1}$, 1338 ±1 cm$^{-1}$, 1336 ±1 cm$^{-1}$, 1183 ±1 cm$^{-1}$, 1103 ±1 cm$^{-1}$, 1099 ±1 cm$^{-1}$, 1020 ±1 cm$^{-1}$, 975 ±1 cm$^{-1}$.

12. The method for determining the quality of a semen according to claim 1, wherein the measuring at least one absorption spectrum comprises preparing said sample from said semen.

13. The method for determining the quality of a semen according to claim 1, further comprising comparing said non-return rate Y with a predetermined threshold, for selecting said semen for reproduction purposes in case where said non-return rate Y is greater than or equal to said predetermined threshold.

14. The method for determining the quality of a semen according to claim 13, wherein the said threshold is greater than or equal to 0.4.

15. The method for determining the quality of a semen according to claim 1, wherein in said measuring, at least 3 absorption spectra of a sample of said seed are measured and said determining values of absorption or of second derivatives of the absorption comprises averaging said measured spectra from which said values of the absorption or the second derivatives of the absorption are determined.

16. The method for determining the quality of a semen according to claim 1, wherein the number n of wave numbers $\sigma_j$ $_{(j\in[1;n])}$ is greater than or equal to 9.

17. The method for determining the quality of a semen according to claim 1, wherein the number n of wave numbers $\sigma_j$ $_{(j\in[1;n])}$ is greater than or equal to 13.

18. The method for determining the quality of a semen according to claim 1, further comprising comparing said non-return rate Y with a predetermined threshold, for selecting said semen for reproduction purposes in case where said non-return rate Y is greater than or equal to said predetermined threshold, wherein the said threshold is greater than or equal to 0.4.

19. The method for determining the quality of a semen according to claim 1, further comprising comparing said non-return rate Y with a predetermined threshold, for selecting said semen for reproduction purposes in case where said non-return rate Y is greater than or equal to said predetermined threshold, wherein the said threshold is greater than or equal to 0.5.

20. The method for determining the quality of a semen according to claim 1, further comprising comparing said non-return rate Y with a predetermined threshold, for selecting said semen for reproduction purposes in case where said non-return rate Y is greater than or equal to said predetermined threshold, wherein the said threshold is greater than or equal to 0.6.

* * * * *